US00PP12722P2

(12) United States Plant Patent
Zerr

(10) Patent No.: US PP12,722 P2
(45) Date of Patent: Jun. 25, 2002

(54) POINSETTIA PLANT NAMED 'FISSON DARK RED'

(75) Inventor: Katharina Zerr, Höhr-Grenzhausen (DE)

(73) Assignee: Floris AG, Binningen (CH)

( * ) Notice: Subject to any disclaimer, the term of this patent is extended or adjusted under 35 U.S.C. 154(b) by 0 days.

(21) Appl. No.: 09/496,459

(22) Filed: Feb. 2, 2000

(51) Int. Cl.[7] ..... A01H 5/00
(52) U.S. Cl. ..... Plt./307
(58) Field of Search ..... Plt./307

(56) References Cited

U.S. PATENT DOCUMENTS

PP9,364 P * 11/1995 Zerr ..... Plt./307
PP9,365 P * 11/1995 Zerr ..... Plt./307
PP9,727 P * 12/1996 Dummen ..... Plt./307
PP10,136 P * 12/1997 Dummen ..... Plt./307
PP11,368 P * 5/2000 Dummen ..... Plt./307

OTHER PUBLICATIONS

German Application for 'FISSON DARK RED' (Dec. 15, 1998).
German Denomination for 'FISSON DARK RED' (Mar. 15, 1999).
Plant Varieties Journal, No. 31 (Apr. 1999), pp. 42–43 (Canada).

* cited by examiner

*Primary Examiner*—Bruce R. Campell
*Assistant Examiner*—June Hwu
(74) *Attorney, Agent, or Firm*—Foley & Lardner

(57) ABSTRACT

A new and distinct cultivar of Poinsettia plant named 'Fisson Dark Red' characterized by having uniform dark-red bract color; medium-sized, star-shaped inflorescence with narrow, slightly lobed bracts; intense dark-green foliage with weak dentation; compact and well-branched, round plant habit; and medium to late flowering.

1 Drawing Sheet

BACKGROUND OF THE INVENTION

The present invention relates to a new and distinct cultivar of poinsettia plant known by the cultivar name 'Fisson Dark Red' and botanically known as *Euphorbia pulcherrima*.

'Fisson Dark Red' is a product of a mutation induction program carried out by the inventor, Katharina Zerr, in Hillscheid, Germany, in 1994. The primary objective of the induction program was to expand the bract color ranges of 'Fisson' (U.S. Plant Pat. No. 9,365). 'Fisson' is characterized by its intense red-colored bracts with strong, pointed lobes, dark-green foliage and relatively compact and bushy habit.

The irradiation program comprised exposing rooted cuttings taken from plants of the parent cultivar to an X-ray source of 30 Gy dosage in Ahrensburg, Germany, under the supervision of the inventor. The irradiated plants were grown out in a greenhouse in Hillscheid, Germany, and were asexually propagated by the inventor by taking cuttings. The plants resulting from these cuttings were screened for mutations as small, flowering, single-stem plants beginning in autumn of 1994 and continuing thereafter. The mutations discovered were identified by numbers. Parts of plants exhibiting a mutation of interest were left to develop vegetative shoots which were used as cuttings and grown out.

'Fisson Dark Red' originated from a single plant (no. 558) displaying distinctly darker red and differently shaped bracts, that was discovered in the late summer of 1995. The apparently completely mutated plant was propagated vegetatively by taking cuttings, and the resulting plants were examined for uniformity in the spring of 1996 prior to further propagation. The clone was examined more closely and compared to the original variety 'Fisson' and to other cultivars in autumn of 1997. Horticultural examination of the clone starting in 1997 and continuing thereafter has confirmed that the combination of characteristics as herein disclosed for 'Fisson Dark Red' are firmly fixed and retained through successive generations of asexual reproduction.

BRIEF DESCRIPTION OF THE INVENTION

The following traits have been repeatedly observed and are determined to be basic characteristics of 'Fisson Dark Red', which in combination distinguish this Poinsettia as a new and distinct cultivar:

1. uniform dark-red bract color;
2. medium-sized, star-shaped inflorescence with narrow, slightly lobed bracts;
3. intense dark-green foliage with weak dentation;
4. compact and well-branched, round plant habit; and
5. medium to late flowering.

'Fisson Dark Red' has not been observed under all possible environmental conditions. The phenotype may vary significantly with variations in environment such as temperature, light intensity, and daylength without any change in the genotype. The following observations, measurements and comparisons describe plants grown in Langley, British Columbia, Canada, under greenhouse conditons which approximate those generally used in commercial practice.

Of the many commercial cultivars known to the inventor, the most similar in comparison to 'Fisson Dark Red' are the parent cultivar 'Fisson' and the co-pending variety 'Fisson Dark Red' (U.S. Plant patent application Ser. No. 09/496,196). In comparison to 'Fisson', 'Fisson Dark Red' has a darker-red bract color, narrower bracts and leaves and a more intense anthocyanin coloration of petioles and stems, and a somewhat more compact plant habit. Plants of 'Fisson Dark Red' were approximately 5 cm shorter and 5–10 cm narrower than plants of 'Fisson'. 'Fisson Dark Red' may take about 7–10 days longer to become marketable, due to the smaller bracts of 'Fisson Dark Red', while the development of the cyathia is almost similar to those of 'Fisson'.

In comparison to 'Fiscor Dark Red', 'Fisson Dark Red' has a somewhat more brillant hue of bract color, narrower bracts and leaves with more distinct lobes, and a narrower plant habit.

BRIEF DESCRIPTION OF THE DRAWING

The accompanying color photographic illustation shows typical inflorescence and foliage of a mature potted plant of 'Fisson Dark Red', with colors being as true as possible with illustrations of this type.

DETAILED BOTANICAL DESCRIPTION

The plants described were grown in a greenhouse in Langley, British Columbia, Canada, in the fall of 1998. Rooted cuttings were planted into 15-cm pots on August 10, and were pinched on August 20, leaving 8 nodes. The minimum temperature was 23° C. until October 10, 20° C. to mid-November, and lower thereafter. The plants initiated flowers under natural short-day conditions in the fall.

Observations and measurements were mainly taken at the beginning of full flowering. In the following description color references are made to The Royal Horticultural Society (R.H.S.) Colour Chart. The color values were determined indoors in a north light.

Classification:

*Botanical.*—*Euphorbia pulcherrima.*

*Commercial.*—Poinsettia, cv. 'Fisson Dark Red'.

Parentage: Induced mutation of 'Fisson'.

Plant:

*Form.*—Shrub, self-branching.

*Growth habit.*—Relatively compact, weak to medium growth, pinched plants are bushy and round in shape.

*Height* (*including 12 cm high pot*).—Approximately 41.8 cm.

*Width.*—48.4 cm.

*Average number of branches.*—9.3.

*Stem color.*—Basic color is green, RHS 137C, partial infusion of anthocyanin creates a brownish hue, RHS 182A.

*Peduncle.*—Light green to green, RHS 143A to RHS 143B, about 6 mm long.

*Rooting.*—Medium, sufficiently rooted for transplanting after about 20–24 days in a greenhouse at a temperature of 22–24° C.

*Blooming habit.*—Flowering response time under natural short day conditions in autumn: botanically (cyathia open) — in early December; commercially (bracts colored, marketable) — in early December.

*Flowering response time.*—About 10–10.5 weeks.

Foliage:

*Shape.*—Ovate to narrow-ovate shaped with acute base, acuminate tip, and with weak to medium distinct, slightly irregularly shaped lobes.

*Edge of margin.*—Entire.

*Texture.*—Upper surface: Smooth, flat and only weakly veined, color of veins is near RHS 146 D; basal part of the midrib may show a similar reddish coloring as the petiole. Lower surface: Flat and smooth, except for the slightly protruding midrib and finer side veins, which protrude at an acute angle from the midrib; the side veins are evenly spread throughout the leaf blade and run parallel to each other; vein color is light green, RHS 145C.

*Size.*—Leaf blade length is 12.6 cm; leaf blade width is 7.9 cm; petiole length is 6.0 cm.

*Color.*—Generally a uniform dark green. Mature foliage: upper surface is RHS 139A. under surface is RHS 137B. New foliage: upper side is about RHS 143A. under side is about RHS 137D.

*Petiole color.*—Dark-red, about RHS 53A.

*Aspect.*—Petioles are horizontally directed, while the leaf blades show slightly downward.

*Disease resistance.*—Typical, no special observations made.

Flowering description:

*Whole inflorescence.*—The bracts are mainly horizontally directed, relatively parallel to the leaf canopy; in the later stages of maturity, the bracts may direct downward.

*Diameter of inflorescence.*—About 25 cm.

*Keeping quality.*—Relatively good.

*Number of bracts per inflorescence.*—7–9 bracts.

*Size of bract.*—Largest true bract is 13.6 cm long and 7.6 cm wide; petiole is 1.5–2.0 cm.

*Bract shape.*—The larger bracts are ovate shaped with acute to rounded base, acuminate tip and weak lobes; the secondary bracts are elliptical with acute base and usually no lobes; the margin of bracts is mainly entire; slight crenation may occur in places.

*Bract texture.*—The blade is often folded along the midrib; its texture is relatively smooth at the beginning of flowering. Later, as bracts mature, veins usually create a somewhat rugose pattern. The arrangement of the veins is similar to that of the leaves. The color of the veins on the upper side corresponds to the dark-red bract color, about RHS 46A, while on the lower side, they appear slightly lighter, about RHS 46D.

*Bract color.*—Generally a brilliant dark-red. Upper surface: Between RHS 46A and RHS 46B. Lower surface: Near RHS 46B.

*Secondary bract.*—Elliptical shape, acute base, very weak lobes, margin entire, crenate in parts; upper surface between RHS 46A and RHS 46B, lower surface near RHS 46B; largest secondary bract 12.6 cm long, next largest secondary bract 9 cm long and 5–6 cm wide.

*Petiole color.*—Dark-red, R.H.S. 53A.

*Cyme.*—About 22 mm wide, few cyathia, about 8–10 in a narrow cluster. Diameter of the single cyathium: 4–5 mm. Color: Mainly light to medium green, RHS 143B, top is dark-red, about RHS 46A–B. Nectar Cups: One nectar cup per cyathium, small to medium sized, 4 mm diameter, 4 mm length, golden yellow, RHS 14A, anthocyanin coloring may occur near the margin, orange RHS 30 A.

Reproductive organs:

*Stamens.*—10–15 in quantity, dark-red filaments, RHS 46A, fertile, yellow pollen, RHS 8 A.

*Pistils.*—Style and stigma are red, near RHS 46B; 6-lobed stigma, trifuracte.

*Ovaries.*—Triangular, 3 ovules, green RHS 143A.

Fruit/seed set: No observations made.

I claim:

1. A new and distinct poinsettia plant named 'Fisson Dark Red', substantially as illustrated and described.

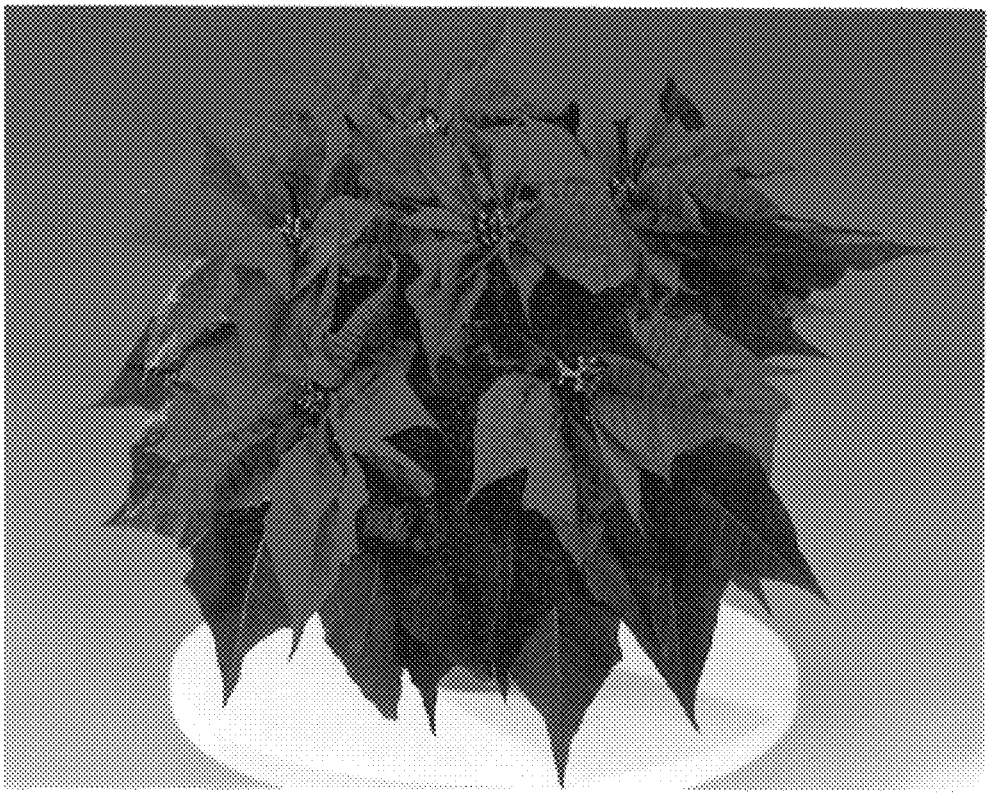

* * * * *